United States Patent [19]

Mody et al.

[11] Patent Number: 5,853,756
[45] Date of Patent: Dec. 29, 1998

[54] CONTROLLED RELEASE FORMULATIONS OF RANITIDINE

[75] Inventors: Shri Shirish Bhagwanlal Mody, Maharashtra; Madhukant Mansukhlal Doshi, Maharashtra; Milind Dattatraya Joshi, Maharashtra, all of India

[73] Assignee: J. B. Chemicals & Pharmaceuticals Limited, Bombay, India

[21] Appl. No.: 522,843

[22] Filed: Sep. 1, 1995

[30] Foreign Application Priority Data

Jan. 11, 1995 [IN] India .................. 17/BOM/95

[51] Int. Cl.⁶ .............. A61K 9/26; A61K 9/58; A61K 9/62
[52] U.S. Cl. .......... 424/451; 424/452; 424/457; 424/458; 424/461; 424/462; 424/468; 424/469; 424/470
[58] Field of Search .................. 424/464, 451, 424/465, 452, 458, 468, 461, 462, 457, 469, 470

[56] References Cited

U.S. PATENT DOCUMENTS 5,407,687  4/1995  Coffin et al. ............ 424/472
5,578,316  11/1996  Bhardwaj et al. ........ 424/441

*Primary Examiner*—Thurman K. Page
*Assistant Examiner*—James M. Spear
*Attorney, Agent, or Firm*—McAulay, Nissen, Goldberg, Kiel, & Hand, LLP

[57] ABSTRACT

The present invention provides oral formulations of Ranitidine Hydrochloride in the form of coated tablets and capsules which produce controlled or regulated dissolution and release at a fairly uniform rate over long periods—as long as 12 to 24 hours—to maintain Ranitidine at desired levels above the MEC.

6 Claims, No Drawings

CONTROLLED RELEASE FORMULATIONS OF RANITIDINE

FIELD OF THE INVENTION

The present invention relates to pharmaceutical formulations which provide controlled release at regulated rates and within desired periods of the pharmacologically useful and active drug Ranitidine Hydrochloride, among others, for anti-ulcer treatment.

BACKGROUND OF THE INVENTION

Ranitidine Hydrochloride is a water soluble drug. It readily dissolves and gets absorbed in the system soon after it is taken orally in the form of a tablet or capsule. Even when oral tablets are sugar coated or film coated in usual fashion, the dissolution and absorption takes places soon after the coating-film or sugar dissolves. As such, the concentration of the drug in the system reaches a peak, then falls rapidly. Even with such increased dosages, the rate of release, and consequently the MEC levels cannot be maintained uniformly or for long periods of time.

For more effective treatment of gastric and intestinal ulcers, it is desirable and necessary to have a formulation which will maintain a level above minimum effective concentration (MEC) and in a regulated manner in the system for longer duration preferably for about 12 to 24 hours. The oral formulations of Ranitidine Hydrochloride presently produced and available are not designed to provide such controlled release. Presently, a drug regimen of two or three doses per day is generally prescribed, and if patient compliance is compromised, and the patient fails to take the second or third dose as prescribed, the efficacy of the treatment may be greatly impaired.

The solution to the problem which exists in current therapy, i.e., to provide a controlled release formulation of Ranitidine, has been a long-felt need in the art. Although methods and substances are generally employed to control the rate of release, dissolution and absorption of different pharmaceutically useful and active pharmaceutical agents, attempts to devise such a formulation for Ranitidine Hydrochloride administration, to date, have been unsuccessful.

The lack of success in providing a solution to this problem may be related to the site, rate and period of release required. Also, the possibility of an adverse, compromising interaction between the active and sustained release polymers may present special problems in the case of Ranitidine Hydrochloride.

OBJECTS OF THE INVENTION

It is an object of the invention to provide an oral formulation of Ranitidine Hydrochloride which exhibits sustained or controlled release characteristics.

It is also an object of the invention to provide an oral formulation of Ranitidine Hydrochloride exhibiting sustained or controlled release characteristics in a coated tablet or capsule form.

These and other objects of the present invention may be readily gleaned from a reading of the description of the invention which follows.

BRIEF DESCRIPTION OF THE INVENTION

The present invention provides oral formulations in the form of coated tablets and capsules which produce controlled or regulated dissolution and release at a fairly uniform rate over long periods—as long as 12 to 24 hours—to maintain Ranitidine at desired levels above the MEC.

In vitro trials have shown that the active agent is released at a controlled rate over long periods which can be extended up to 24 hours.

The controlled release oral formulations of the present invention may be prepared by the following process:

i) To a weighed quantity (taken proportionately relative to the dose of the active drug in the final formulation) of Ranitidine Hydrochloride, are added required quantities of the specified polymer and the other necessary excipients and solvents, and the mass is thoroughly mixed and blended to make a uniform paste, which is thereafter dried and granulated.

For Coated tablets the following general procedure is used:

ii) For formulations in the form of coated tablets, the granules so obtained are compressed into tablets of a weight and size which is adjusted to give the required dose of the active drug, adding lubricants or binding agents as required, and the tablets obtained are checked for in-process control tests such as dissolution rate, weight, appearance and the other relevant quality attributes, and the tested and approved tablets are thereafter coated. The coating may optionally contain a specified polymer. The coated tablets so obtained are subjected to quality control tests including a drug release test in compliance with the established release requirements.

For formulations in capsule form, the following general procedure is used:

iii) For formulations in the form of capsules, the granules obtained as per (i) above may optionally be coated with a coating solution containing a specified polymer depending on the rate and time of release desired. The required quantity of coated granules so obtained are then filled and encapsulated in capsules, and tested for quality standards. The rate and time of dissolution of the active drug is also checked.

The excipients and solvents required to be used at various stages of the process are selected from pharmaceutically acceptable excipients normally employed in pharmaceutical formulation. Those skilled in the art can decide as to the particular excipients and solvents and quantities thereof to be employed in the process, having regard for the quantity of the active drug to be taken, and rates and periods of release of the active drug desired in the final formulation.

The expression "Specified Polymer" as used in this specification refers to any one or more of the pharmaceutically accepted inert polymer or mixture of such polymers normally employed and described in literature for coating of drugs for controlled release, out of which, the polymers alkyl-celluloses such as methylcellulose and ethylcellulose, polyvinylpyrrolidone, hydroxymethylcellulose, hydroxypropylcellulose, hydroxypropylmethyl cellulose, (available under the Trade Names Methocel K4M, K115M, K100M, or E, J, F grades) and sodium carboxymethylcellulose, are the preferred polymers. The other specified polymers which may also be used for the process are polyethylene glycol, and such other polymers generally used, including modified polymethacrylate copolymers (including methyl methacrylate copolymers sold under the trade name "Eudragit") of varying permeability. Various grades of these methacrylate polymers, including mixtures, may also be used in the instant invention so as to yield controlled release pharmaceutical formulations of Ranitidine hydrochloride.

The quantity of the specified polymer to be taken for blending (stage (i) above) ranges from about 0.2 to 1.2 by weight of the active drug used with the quantity of the active drug taken, the particular proportion and quantity of polymer to be, determined without undue experimention by one of ordinary skill in the art with reference to the rate and time of release of the active drug desired in the final formulation.

The best results are obtained using the preferred polymers' mentioned above, with a more preferred group of polymers being the cellulose polymers, in particular hydroxymethyl cellulose, hydroxypropyl cellulose, hydroxypropylmethyl cellulose and sodium carboxymethylcellulose, with hydroxypropylmethyl cellulose being particularly preferred. Mixtures of low and high molecular weight specified polymers may also be used to obtain a preferred release of the active agent. In this regard, a mixture of low molecular weight hydroxypropylmethyl cellulose and high molecular weight hydroxyproylmethyl cellulose is preferred to provide particularly useful sustained or controlled release formulations of Ranitidine Hydrochloride.

The solvents to be used for the formulation process are pharmaceutically acceptable solvents, with particular solvents being selected on basis of the solubility of the polymer and the drug employed. The solvent is suitably selected from water, alcohols, including ethyl alcohol, methanol, isopropanol, butanol and isobutanol, ketones, halogenated aliphatic compounds, halogenated aromatic hydrocarbon compounds, aromatic hydrocarbon compounds and cyclic ethers or a mixture thereof. Preferred solvents for use in the present process include, for example, water, hexane, heptane, methanol, ethanol, isopropyl alcohol, acetone, methylethyl ketone, methylisobutyl ketone, methylene chloride, chloroform, carbon tetrachloride, toluene, xylene and tetrahydrofuran, and mixtures thereof, among others.

The process as described in this specification yields the tablet/capsule formulations with controlled or sustained rate of delivery of the active drug.

The following examples are provided to illustrate the present invention and should not be misunderstood to limit the scope of the present invention in any way.

EXAMPLE 1

Ranitidine Hydrochloride 336.0 g equivalent to Ranitidine 300 g is mixed with Hydroxypropylmethyl cellulose K 15M—77.0 g. and Hydroxypropylmethyl Cellulose K 100M—35.0 g. in the presence of the solvents Isopropyl alcohol (500 ml) and methylene chloride (300 ml.). The granules were dried and then tabletted with the aid of Magnesium Stearate (2 g) as a lubricant, to obtain a tablet equivalent to 300 mg of active ingredient, and having controlled rate of dissolution and drug release as desired.

The compressed tablets as prepared above were further coated with a coating solution consisting of:

Hydroxypropylmethyl cellulose . . . 2.0 g
Polyethylene glycol . . . 1.0 g
Titanium Dioxide . . . 0.2 g
Methylene chloride (25 ml)
Isopropyl alcohol (25 ml)

In the above Example, the ratio of Ranitidine Hydrochloride, Hydroxypropylmethyl cellulose K 15M and Hydroxypropylmethyl cellulose K 100M may also be suitably altered within the previously desribed weight range limits, which while retaining the characteristic nature of the drug, may provide release of the effective drug at a different rate and period as may be desired. This concept also applies in the case of the subsequent examples.

EXAMPLE 2

Ranitidine Hydrochloride 168.0 g (equivalent to Ranitidine 150 g) is mixed with Hydroxypropylmethyl cellulose K 15M—50.0 g. and Hydroxypropylmethyl cellulose K 100M—62.0 g. in the presence of solvents Isopropyl alcohol (500 ml) and methylene chloride (300 ml.). After mixing, the granules were dried and then tabletted with the aid of Magnesium Stearate (2 g) as a lubricant, to obtain a tablet containing the equivalent of 150 mg of active ingredient, and having a rate of dissolution and drug release as desired.

The compressed tablets were further coated with a coating solution consisting of:

Hydroxypropylmethyl cellulose . . . 2.0 g
Polyethylene glycol . . . 1.0 g
Titanium Dioxide . . . 0.2 g
Methylene chloride (25 ml)
Isopropyl alcohol (25 ml)

EXAMPLE 3

Ranitidine Hydrochloride 336.0 g (equivalent to Ranitidine 300 g) is mixed and granulated with Hydroxypropylmethyl cellulose K 15M—75.0 g. and Hydroxypropylmethyl cellulose K 100M—37.0 g. in the presence of solvents Isopropyl alcohol (500 ml) and methylene chloride (300 ml.).

The granules so obtained were further coated with a coating solution consisting of:

HydroxypropylMethyl cellulose . . . 2.0 g
Polyethylene glycol . . . 1.0 g
Titanium Dioxide . . . 0.2 g
Methylene chloride (25 ml)
Isopropyl alcohol (25 ml)

The coated granules were then encapsulated in a conventional manner to obtain capsules containing 300 mg of active ingredient, and having controlled rate of dissolution and drug release as desired.

EXAMPLE 4

The procedure employed was similar to that in Example 1 except that the amount of Hydroxypropylmethyl cellulose K-15M taken was 75 g and also included was sodium carboxymethyl cellulose (5 g).

EXAMPLE 5

The procedure employed was similar to that in Example 1 except that the Hydroxypropylmethyl cellulose K 15M was replaced by methylmethacrylates (75 g) (Eudragit).

EXAMPLE 6

The procedure employed was similar to that in Example 1 except that polyvinylpyrrolidone was used instead of Hydroxypropyl methylcellulose,K 15M.

The formulations obtained utilizing the previously described procedures as described in each of the above examples, when tested in vitro, show release of the active drug in a controlled manner for maintaining MEC levels over longer duration ranging from 12 hours to 24 hours.

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

We claim:

1. An oral pharmaceutical formulation of Ranitidine Hydrochloride in capsule form, said formulation comprising granules containing a therapeutically effective amount of Ranitidine Hydrochloride in combination with a specified polymer which are coated with a coating comprising a specified polymer and encapsulated, said specified polymer in said coating and said granules being selected from the group consisting of alkyl celluloses. hydroxymethylcellulose, hydroxypropylcellulose, hydroxypropylmethylcellulose, sodium carboxymethylcellulose, polyvinylpyrrolidone, polyethylene glycol, polymethacrylate copolymers, and mixtures, thereof, said polymer being included in said granules taken in quantity equivalent to about 0.2 to about 1.2 times the weight of said Ranitidine Hydrochloride, said oral pharmaceutical formulation providing a minimum effective concentration of Ranitidine Hydrochloride for a sustained period of at least about 12 hours.

2. The formulation according to claim 1 wherein said specified polymer is selected from the group consisting of alkyl celluloses, polyvinylpyrrolidone, polymethacrylate copolymers, polyethylene glycol, and mixtures, thereof.

3. The formulation according to claim 1 wherein said specified polymer is selected from the group consisting of methylcellulose, ethylcellulose, hydroxymethylcellulose, hydroxypropylcellulose, hydroxypropylmethyl cellulose, sodium carboxymethylcellulose, polyvinylpyrrolidone and mixtures, thereof.

4. The formulation according to claim 1 wherein said amount of Ranitidine Hydrochloride taken is equivalent to about 150 mg or about 300 mg Ranitidine.

5. An oral pharmaceutical formulation of Ranitidine Hydrochloride in tablet or capsule form, said formulation comprising a therapeutically effective amount of Rantidine Hydrochloride in combination with at least one specified polymer selected from the group consisting of hydroxymethylcellulose, hydroxypropylcellulose, hydroxypropylmethylcellulose, sodium carboxymethylcellulose and mixtures, thereof, in granules, said specified polymer taken in quantity equivalent to about 0.2 to about 1.2 times the weight of said Ranitidine Hydrochloride taken, said oral pharmaceutical formulation providing a minimum effective concentration of Ranitidine hydrochloride for a sustained period of at least about 12 hours.

6. The formulation according to claim 5 wherein said polymer is a mixture of two hydroxypropylmethylcellulose polymers of two different molecular weights.

* * * * *